(12) United States Patent
Mullani

(10) Patent No.: US 7,167,244 B2
(45) Date of Patent: *Jan. 23, 2007

(54) DERMOSCOPY EPILUMINESCENCE DEVICE EMPLOYING MULTIPLE COLOR ILLUMINATION SOURCES

(75) Inventor: Nizar A. Mullani, Sugar Land, TX (US)

(73) Assignee: 3gen, LLC., Dana Point, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/361,432

(22) Filed: Feb. 24, 2006

(65) Prior Publication Data

US 2006/0139640 A1 Jun. 29, 2006

Related U.S. Application Data

(63) Continuation of application No. 10/773,003, filed on Feb. 5, 2004, now Pat. No. 7,027,153, which is a continuation-in-part of application No. 10/384,110, filed on Mar. 7, 2003, now Pat. No. 7,006,223.

(51) Int. Cl.
*G01J 4/00* (2006.01)

(52) U.S. Cl. .......................... 356/369; 600/476; 606/9

(58) Field of Classification Search ........ 356/364–369, 356/445–448, 39; 600/9, 306, 340, 476, 600/477; 362/19, 138–140; 359/501, 493, 359/368, 385, 390
See application file for complete search history.

(56) References Cited

U.S. PATENT DOCUMENTS 2,120,365 A 6/1938 Kriebel (Continued)

FOREIGN PATENT DOCUMENTS

IT 01300568 10/1999

OTHER PUBLICATIONS

Keshen R. Mathura et al., "Comparison of OPS imaging and conventional capillary microscopy to study the human microcirculation," p. 74-78 The American Physiological Society, 2001.

(Continued)

*Primary Examiner*—Hoa Q. Pham
(74) *Attorney, Agent, or Firm*—Stetina Brunda Garred & Brucker

(57) ABSTRACT

The present invention provides a hand held dermoscopy epiluminescense device having a generally circular optical magnification lens incorporated into the housing of the device. A lighting array provides the light necessary for medical examination of the skin. The lighting array comprises a ring of LEDs comprising four different colored sets of LEDs each on a different lighting circuit. The four colors comprise White, UV/Blue (405 nm), green/yellow (565 nm) and orange/red (630 nm). A second embodiment provides a hand held dermoscopy epiluminescense device with a magnification lens and an associated ring of luminous diodes powered by an on board battery. Every other diode in the ring operates as first and second light sources. The even diodes are filtered by a first polarization ring and the odd diodes are filtered by a second polarization ring. Each polarization ring has an open center for the lens and openings sized and positioned to correspond to the even or odd diodes to only filter one set. A viewing polarizer is provided and is cross-polarized relative to the first polarization ring and is parallel-polarized with the second polarization ring. The device is threaded to mate with a camera or camera lens.

24 Claims, 12 Drawing Sheets

U.S. PATENT DOCUMENTS

| | | |
|---|---|---|
| 2,866,375 A | 12/1958 | Wells et al. |
| 2,947,212 A | 8/1960 | Woods |
| 3,062,087 A | 11/1962 | Zandman et al. |
| 3,711,182 A * | 1/1973 | Jasgur ..................... 359/493 |
| 4,007,979 A | 2/1977 | Coblitz |
| 4,398,541 A | 8/1983 | Pugliese |
| 4,773,097 A | 9/1988 | Suzaki et al. |
| 4,846,184 A | 7/1989 | Comment et al. |
| 4,957,368 A | 9/1990 | Smith |
| 4,998,818 A | 3/1991 | Kugler et al. |
| 5,146,923 A | 9/1992 | Dhawan |
| 5,198,875 A | 3/1993 | Bazin et al. |
| 5,343,536 A | 8/1994 | Groh |
| 5,363,854 A | 11/1994 | Martens et al. |
| 5,690,417 A | 11/1997 | Polidor et al. |
| 5,742,392 A | 4/1998 | Anderson et al. |
| 6,032,071 A | 2/2000 | Binder |
| 6,069,565 A | 5/2000 | Stern et al. |
| 6,081,612 A | 6/2000 | Gutkowicz-Krusin et al. |
| 6,118,476 A * | 9/2000 | Morito et al. .................. 348/65 |
| 6,207,136 B1 | 3/2001 | Matsuoka |
| 6,384,988 B1 | 5/2002 | Muller et al. |
| 6,483,247 B2 | 11/2002 | Edwards et al. |
| 6,587,711 B1 | 7/2003 | Alfano et al. |
| 7,004,599 B2 * | 2/2006 | Mullani ..................... 362/139 |
| 7,006,223 B2 * | 2/2006 | Mullani ..................... 356/369 |
| 7,027,153 B2 * | 4/2006 | Mullani ..................... 356/369 |
| 2003/0026110 A1 | 2/2003 | Satoh et al. |
| 2003/0045799 A1 | 3/2003 | Bazin et al. |

OTHER PUBLICATIONS (Brochure) 3gen, LLC., "First in Pocket Epiluminescence Microscopy," 1 page, Mar. 15, 2001 (Estimated publication date).

(Brochure) 3gen, LLC., "3gen the Beauty of Evolutionary Innovation," 3 pages (trifold), Feb. 15, 2002 (Estimated publication date).

(Internet Literature) www.syrissscientific.com, "Technical", 1 page, (Unknown publication date).

\* cited by examiner

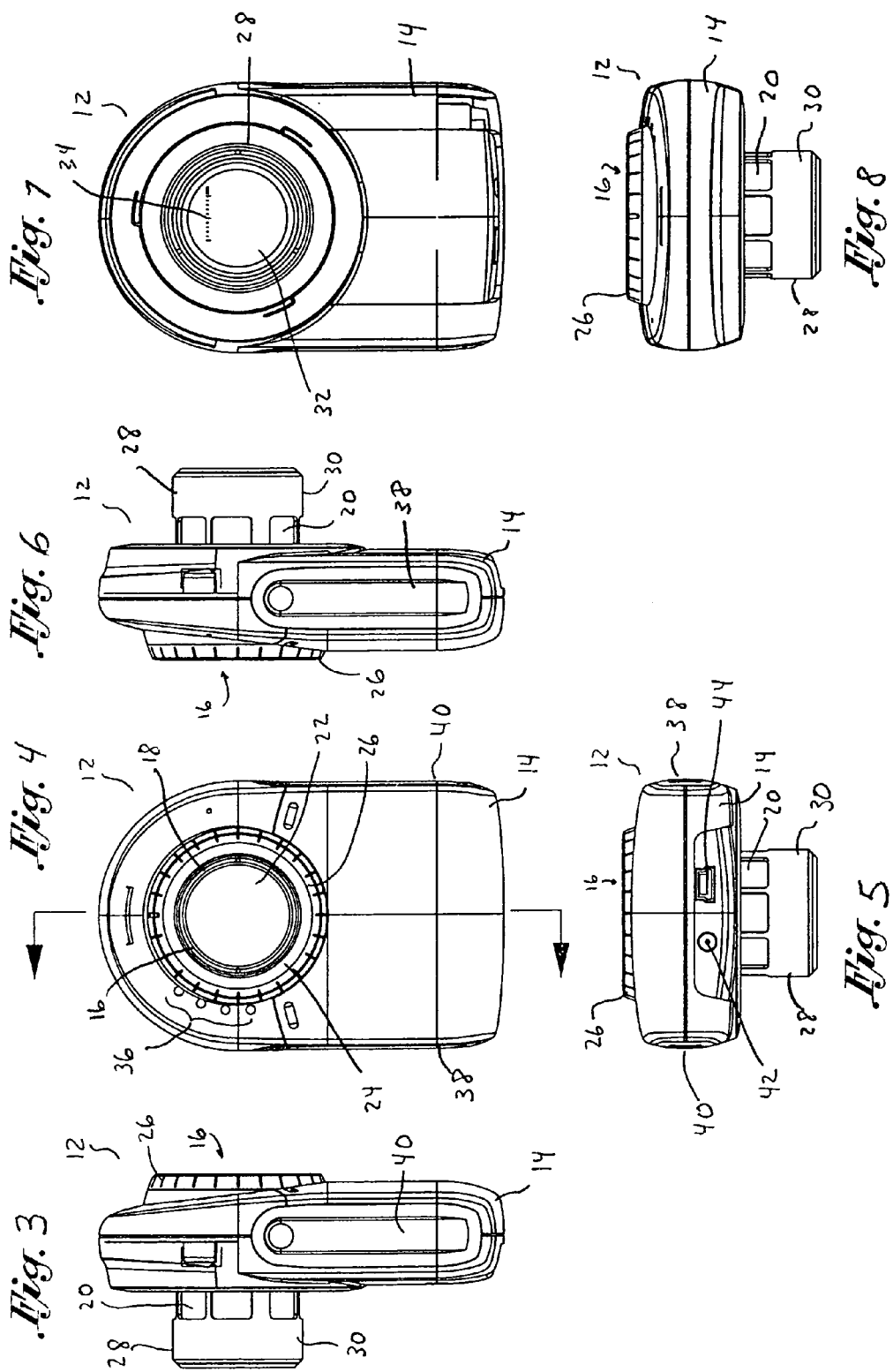

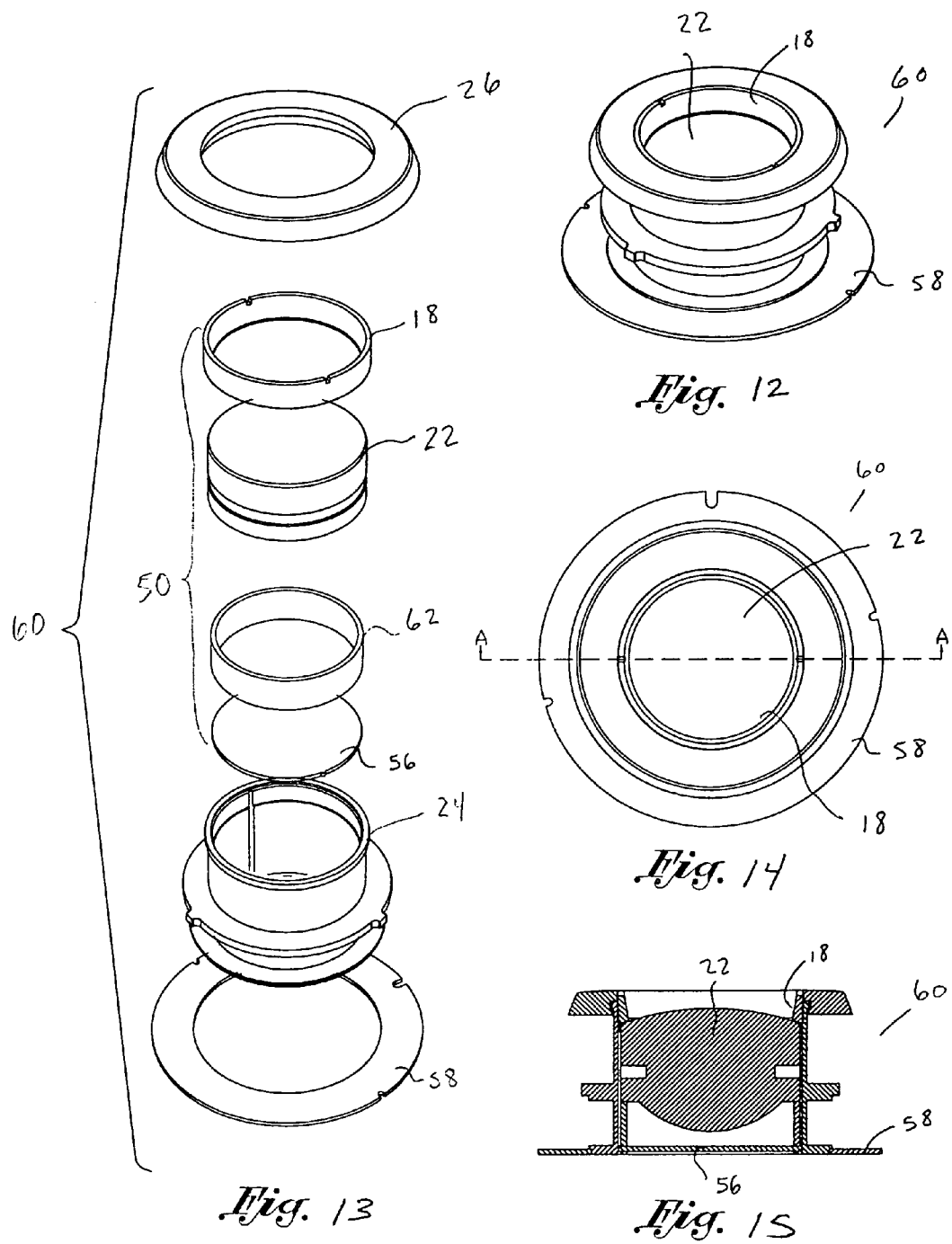

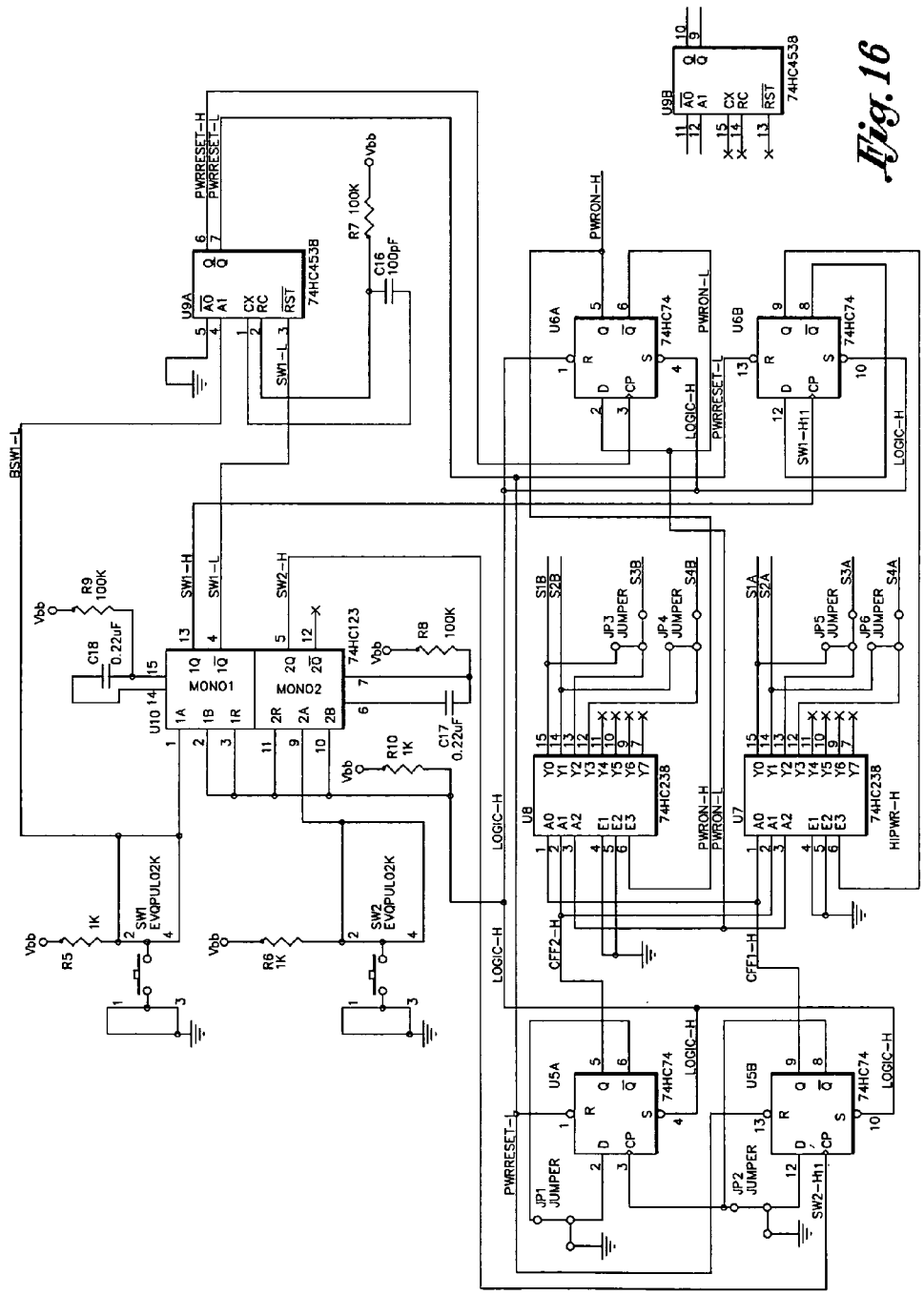

spacer extended spacer retracted spacer extended

DERMOSCOPY EPILUMINESCENCE DEVICE EMPLOYING MULTIPLE COLOR ILLUMINATION SOURCES

CROSS-REFERENCE TO RELATED APPLICATIONS

The present application is a continuation application of U.S. patent application Ser. No. 10/773,003 filed Feb. 5, 2004 and issued Apr. 11, 2006 as U.S. Pat. No. 7,027,153, the substance of which is incorporated herein by reference, which is a continuation-in-part of U.S. patent application Ser. No. 10/384,110 filed Mar. 7, 2003 and issued Feb. 28, 2006 as U.S. Pat. No. 7,006,223 entitled Dermoscopy Epiluminescence Device Employing Cross and Parallel Polarization, the substance of which is relied upon and incorporated herein by reference.

STATEMENT RE: FEDERALLY SPONSORED RESEARCH/DEVELOPMENT

Not Applicable.

FIELD OF THE INVENTION

The present invention relates generally to an epiluminescence device used in dermoscopy. More particularly, the invention comprises an improved apparatus for illuminating the skin for medical examination by providing multiple colored light sources to aid in viewing and treatment of the skin.

BACKGROUND OF THE INVENTION

Dermoscopy is the term used to describe methods of imaging skin lesions. Skin is the largest organ in the body and it is the most easily accessible organ for external optical imaging. For early detection of cancers, it is important that the skin be medically examined for lesions.

With over forty (40%) percent of the cancers occurring on the skin (American Cancer Society Statistics 2001, Perelman 1995), and incidence of skin cancer increasing each year, tools and methods of imaging skin lesions are becoming increasingly important. Most of the cancers detected on the skin are Basal Cell Carcinoma (BCC) and Squamous Cell Carcinoma (SSC), which are differentiated from melanoma, a more deadly form of skin cancer. The early detection of skin cancer allows for inexpensive treatment before the cancer causes more severe medical conditions. Thus, there is a great need in the art for simple inexpensive instruments that allow for the early screening for skin cancer.

Because skin is partially translucent, dermoscopy utilizes tools for visualization of the pigmentation of the skin below the surface. In this regard, when attempting to visualize the deeper structure of the skin, it is important to reduce the reflection of light from the skin that may obscure the underlying structures. Methods used to reduce the surface reflection from the skin are referred to as epiluminescence imaging. There are three known methods for epiluminescence imaging of the skin, oil-immersion, cross-polarization, and side-transillumination. Oil-immersion and cross-polarization methods have been extensively validated for early skin cancer detection while side transillumination methods are currently undergoing study and clinical validation.

Oil-immersion devices are generally referred to as Dermatoscopes. Dermatoscopes permit increased visualization of subsurface pigmentation by using a magnification device in association with a light source. In operation, oil is placed between the skin and a glass faceplate. The placement of oil and a glass interface between the eye and the surface of the skin reduces the reflected light from the skin, resulting in deeper visualization of the underlying skin structure.

While oil-immersion has proved to be an excellent method of epiluminescence imaging of the skin, demonstrating improved sensitivity for melanoma detection, it is messy and time consuming for the physician. As a result, the Dermatoscope is used mostly by physicians that specialize in pigmented lesions and for evaluation of suspicious lesions that cannot be diagnosed visually. Also, the oil-immersion of the Dermatoscope has been found to be less effective for BCC and SCC imaging. The pressure created by the compression of the glass faceplate causes blanching of blood vessels in the skin resulting in reduced capability of the Dermatoscope for imaging the telangiectesia that is often associated with BCC or other malignant lesions.

Cross-polarization or orthogonal polarization is another method of reducing the reflection of the light from the surface of the skin to aid in the medical examination of the skin. Light emanating from a light source is first linearly polarized, so that the orientation of the light falling on the skin surface is in the same plane of polarization. As the light enters the skin, its polarization angle changes such that the light is reflected from a deeper structure. However, the light reflected from the surface of the skin is still polarized in the same plane as the incident light. By including a second polarizer in the path of the reflected light from the skin, a selective filtering of light can be achieved.

Most of the light directed to the skin's surface is reflected, as the refractive index of skin is higher than that of air. The reflection of light, off of the skin, is analogous to the reflection of light off of the surface of water. Accordingly, the information received by the eye carries mostly information about the contour of the skin surface rather than the deeper structures. Remaining light enters the skin and is absorbed or is reflected back in a scattered fashion. By polarizing the incident light with a second polarizer, the specular component of the reflected light is blocked by the viewing polarizer, thus producing an enhanced view below the skin surface. Accordingly, inflammation, color, pigmentation, hair follicles, blood vessels and other structures may be viewed.

When the incident light and the second polarizer are parallel, the surface topography and properties of the skin are highlighted and enhanced. In this regard, if the polarizer in the path of the light from the skin to the eye is polarized in the same orientation of the incident light, only the light from its polarization angle will be allowed to pass through the lens. Cross-polarization imaging of the body was originally described by R. R. Anderson ("Polarized light examination and photography of the skin." Archives Dermatology 1991; 127; 1000–1005). Later, Binder introduced the MoleMax manufactured by Derma Instruments (Vienna, Austria) for the examination and mapping of pigmented lesions. Binder further developed the no-oil cross-polarization epiluminescence method. MoleMax, however, while validating clinically the improved diagnosis and accuracy without the use of oil, still used a glass faceplate and video imaging system to execute skin examinations.

In light of many of the difficulties associated with prior dermoscopy systems, simple and cost-effective diagnostic systems remained unavailable for general dermatologists to use on a routine clinical basis. Dermoscopy, until recently, remained generally a research tool utilized in special clinical cases. More recently, however, a substantial advancement in skin cancer detection occurred through a simple device identified as DermLite®, manufactured and marketed by 3Gen, LLC, Monarch Beach, Calif. With the low cost and ease of use of the DermLite® Device, screening for cancer by dermatologists, in routine clinical examination of skin disease, has become a reality. The DermLite® device uses cross-polarization epiluminescence imaging through use of white light emitting diodes (LEDs), a high magnification lens (10×), and a lithium ion battery contained in a small lightweight device.

In the DermLite® device, a window is incorporated into a compact housing, and a plurality of white light LEDs encircle a magnifying lens. The DermLite® device incorporates cross-polarization filters that reduce the reflection of light from the surface of the skin and permits visualization of the deeper skin structures. Light from eight (8) LEDs is polarized linearly by a polarizer, which is annular in shape and located in front of the LEDs. The imaging viewed through the magnifying lens is also linearly polarized by using a polarizer that is located in front of the lens. The LEDs have a narrow beam angle that concentrates the light into a small area, pointing the incident light to the center to increase the brightness of the area being viewed. Thus, light from the LEDs passes through the polarizer which enters the skin and reflects back through the viewing polarizer to create cross-polarization allowing examination to look deeper within the skin structure. Although, the DermLite® product has been recognized as a major advancement in the art of routing clinical diagnosis and analysis of skin cancer lesions, DermLite® device does not provide a mechanism for enabling the user to additionally view parallel-polarized light, or a combination of cross-polarized light and parallel-polarized light. The DermLite® Platinum™ product, also manufactured by 3Gen, LLC., was developed to provide variable polarization. In the Dermlite® Platinum™, a rotating dial achieves variable polarization. Rotation of the polarizer to a cross-polarization cancels out the surface reflection for an in-depth look at the deeper pigmentation in lesion structure. Rotation to parallel polarization allows a clear view of the skin surface. The DermLite® Platinum™ product requires manual manipulation of the dial which may cause user to lose the viewing spot, or otherwise interfere with examination. Further, DermLite®Platinum™ does not provide a user the ability to view the skin with an instantaneous switch over from cross-polarization to parallel polarization.

The DermLite®Pro DP-R™ also manufactured by 3gen, LLC, was developed to provide instant, button activated, polarization control. Embodiments of the DermLite® Pro DP-R™ are disclosed in U.S. patent application Ser. No. 10/384,110 filed Mar. 7, 2003, the substance of which is incorporated by reference. Variable mode polarization is provided by a toggle switch that allows the viewer to view the surface of the skin using a polarizing mode, and a switch mode, and a switch creates a cross-polarization which cancels out surface reflection for a view of the deeper pigmentation and structures of the skin.

While existing devices have been proven for effectiveness in detecting melanomas, non-melanoma skin cancers (NMSC) such as BCC and SSC have little or no melanin and therefore are very hard to detect by classical dermoscopy methods. Detection of NMSC is usually carried out by visually examining the suspected reddish areas of skin eruptions with a magnifying lens. Early NMSC are usually detected by looking for the presence of abnormal blood vessels, which are best seen with an epiluminescence device that does not use a glass faceplate and oil. The presence of a glass faceplate and oil blanches the blood vessels and makes it difficult to see the increased vascularity. In addition, NMSC excision boundaries are very difficult to estimate without the information about the subsurface extension of the lesion. Kumar et al (2002) [inset cite] examined 757 BCC that were excised in a British hospital and found positive margins in 3.1% to 7.5% of the excisions, depending on the location of the lesion. Another study by Hallock et al (2001) [Hallock G G, Lutz D A, 2001, A Prospective Study of the Accuracy of the Surgeon's Diagnosis and Significance of Positive Margins in Non-Melanoma Skin Cancers. Plast Reconstr Surg 107:942–7]examined the incidence of positive margins in excised lesions from a private clinic. They found that 20% of all the excisions were malignant (98% were NMSC) and that within the malignant group, 15.7% of the NMSC had positive margins. In this study, 80% of all the excisions were not malignant. Both studies show a significant percentage of excisions with positive margins using present methods.

The presence of positive margins could contribute in part to the recurrence of NMSC. In Australia, where the incidence of BCC and SCC is extremely high (3% as reported by Diepgen et al (2002)), recurrence of NMSC, as reported in a three (3) year study by Czarnecki et al (1996), is 8%. The incidence of multiple NMSC in Australian population was found to be 38.5%, as published in a large study by Raasch et al (2002). And, in a 10 years study by Czarnecki et al (2002), the incidence of second skin cancer occurred in 67.8% of the study population with very high odds for malignant melanoma in the NMSC patients. Incomplete excision can result in recurrence of disease at the same site. And, once the skin lesion becomes larger and is located on the face, normal excisions cannot be performed. Instead, a costly procedure called Mohs Microsurgery (MMS) needs to be performed to remove only the minimum amount of normal tissue. Welch et al (1996) studied the incidence of MMS in 5193 NMSC over a five years period. They found that 32.7% of the NMSC had MMS surgery during the five-year period.

NMSC are characterized by reddish fleshy (nodular) or flat (sclerosing) areas on the skin. These skin lesions usually grow from a pinpoint-sized object, that looks like a pimple, to as large as several mm in size. NMSC are usually found on the head and the neck areas. Ceylan et al (2003) [Ceylan C., Ozturk G, Alpers S., 2003 Non-melanoma Skin Cancers Between the Years of 1990 and 1999 in Izmir, Turkey: Demographic and Clinicopathological Characteristics. J. Dermaol 30:123–31] showed, in a Turkish population, that 46.6% of the NMSC were located on the face, and that 78.4% of the lesions were between 11 and 20 mm in size at the time of diagnosis.

The visual features that make NMSC different from surrounding normal skin are the abnormal blood vessels and increased vascularity of the lesion. Bedlow et al (2003) [Bedlow A J, Stanton A W, Cliff S., Mortimer P S. Basal Cell Carcinoma and In-vivo Model of Human Tumor Microcirculation? Exp Dermatol 1999, 8:222-6], using video capillaroscopy for the examination of blood vessels in situ, showed that the superficial blood vessels in the BCC are larger and longer than normal blood vessels. They computed the ratio of BCC vessels to normal vessels and found that the area of the BCC vessel was 4.9 times larger and the length was 5.9 times longer than for normal vessels. Weninger et al (1997) [Weninger W, Rendl M, Pammer J, Grin W, et al 1997. Differences in Tumor Microvessel Density Between Squamous Cell Carcinomas and Basal Cell Carcinomas May Relate to Their Different Biological Behavior. J Cutan Pathol 24:364–9] found that SCC had larger vascularity than normal tissue in a study that examined microvessel density (MVD) in excised tissue. Stanton et al (2003) [Stanton A W, Drysdale S B, Patel R, Mellor R H et al. 2003. Expansion of Microvascular Bed and Increased Solute Flux in Human Basal Cell Carcinoma In-Vivo, Measured by Fluorescein Video Angiography. Cancer Res 63:3969–79] used laser Doppler flow and video microscopy with injections of fluorescein to study BCC in vivo. They found increased vasculature and blood flow in BCC. Increased number of blood vessels and larger sized blood vessels means a larger blood volume, which is usually associated with increased blood flow in malignant lesions. Accordingly, finding an inexpensive means to view and analyze these features is therefore important in the field.

Recent discoveries in optical fluorescence imaging have identified several molecules having fluorescence properties that are useful in medicine and in particular, dermatology. Simple applications such as delta-aminolaevulinic acid (ALA) applied topically have been found to enhance the visualization of basal cell cancer from normal tissue, when illuminated with UV/Blue light. Fluorescein is another fluorescent compound that has been in clinical use in opthamology for several years and has great potential for use in dermatological applications. Indocyanine green (ICG), Methylene Blue, and ethyl nile blue are contrast agents that are used to increase light absorption in blood vessels. There are several FDA approved optical fluorescence tracers already approved for clinical use, and several more new probes may be applicable in the future. However, the use of fluorescence imaging of the skin has been illusive for clinical dermatologist because of the complexity and costs of the associated equipment.

In current applications, such as in the application of ALA topically to a basal cell carcinoma to a BCC, conventional white light visual images of the BCC are displayed next to the fluorescence excited images of ALA in the BCC. The ALA is taken up by the active areas of cancer, converted to porphyrin IX, and fluoresces when exposed to UV/Blue light. It becomes apparent that the fluorescent areas of the BCC may not coincide with the anatomical features of the BCC as shown in white light. Currently the side-by-side comparison is only available by taking two separate images and co-registering these images later in the computer.

Thus, there is a great need in the art for a device that will allow clinical viewing of skin lesions which provides on demand switching that can toggle back and forth from a white light to a colored or UV light in order to contrast and compare images. Further there is a great need in the art for a device to allow the clinical viewing of skin lesions that provides on demand switching that can toggle between from lights of differing wavelengths or colors. Further there is a great need in the art to allow the on-demand comparison images of the skin illuminated by differing wavelengths viewed in combination with cross and parallel polarization.

BRIEF SUMMARY OF THE INVENTION

The present invention relates to a dermoscopy epiluminescence device used in the medical diagnosis of skin lesions. The device is a hand held modular housing incorporating a magnification lens and associated lighting scheme for examining the epidermis on humans. The light sources of the lighting scheme are powered by an on board lithium battery and are controlled by a switches that provide on demand use of four differently colored cross-polarized light sources for epiluminescence. The switching of the light colors can also be controlled remotely using a USB connection and an onboard microprocessor.

More particularly, a first embodiment of the present invention comprises a generally circular optical lens incorporated into the housing of the device. The lens produces a magnified image of the skin to be observed by a viewer. In the first embodiment the lens is a 25 mm diameter lens with a 10× optical gain. The viewer observes the magnified skin through the lens window of the housing. The viewing is aided by a plurality of luminous diodes positioned within the housing and about the circumference of the lens. The diodes direct light upon the skin to be viewed. The LEDs are staggered into four sets with each set having a differing color wavelength. There are a total of 32 LEDs, grouped in four sets of eight LEDs each. Four light circuits form first, second, third and fourth illumination sources forming a ring of staggered diodes about the lens. Two switches are provided that when not in operation have a normal OFF mode. In operation, a first switch powers ON/OFF the device, and a second switch selects between the one of the four LED groups. The first switch also can select between high and low settings of the lights.

A first polarizer filter comprises a planar annular ring defining a generally circular center opening and an outer ring. The center opening of the annular ring of the first polarizer is positioned in alignment with the circular optical lens to provide an unobstructed view of the skin through the lens and the housing. The outer ring of the first polarizer filter polarizes light emitted from each of the LEDs.

A viewing polarizer is also provided positioned in the housing in line with viewing corridor of the optical lens. The viewing polarizer filters light reflected back from the skin and is cross-polarized relative to said first polarizer and is parallel-polarized relative to said second illumination source. The cross-polarization aids the examiner in viewing deeper structures of the skin while the parallel polarization aids in viewing the topography of the skin.

In a second embodiment of the invention, the device comprises a generally circular optical lens incorporated into the housing of the device. The lens produces a magnified image of the skin to be observed by a viewer. The viewer observes the magnified skin through the lens window of the housing. The viewing is aided by a plurality of luminous diodes positioned within the housing and about the circumference of the lens. The diodes direct light upon the skin to be viewed. Two light circuits form first and second illumination sources forming a ring of alternating diodes about the lens. A first polarizer filter comprises a planar annular ring defining a generally circular center opening and an outer ring. The center opening of the annular ring of the first polarizer is positioned in alignment with the circular optical lens to provide an unobstructed view of the skin through the lens and the housing. The outer ring of the first polarizer includes a plurality of openings sized and positioned to correspond to the diodes of the second illumination source (i.e. every other diode of the second light circuit) such that light emitted from the diodes of the second illumination source passes through the openings unfiltered by the first polarizer. Because there are no corresponding openings for the diodes of the first illumination source (i.e. every other diode on the first light circuit) light emitted from first source diodes is polarized by the outer ring of the first polarizer filter.

A second polarizer filter comprises a planar annular ring defining a generally circular center opening and an outer ring. The center opening of said annular ring of the second polarizer is positioned in alignment with the circular optical lens to provide an unobstructed view of the skin through the lens and housing. The second polarizer is 90 degrees out of phase with the first polarizer. The outer ring of the second polarizer has a plurality of openings sized and positioned to correspond to the diodes of the first illumination source (i.e. every other diode on the first light circuit) such that light emitted from the diodes of the first illumination source passes through the openings unfiltered by the second polarizer. Because there are no corresponding openings for the diodes of the second illumination source (i.e. every other diode on the second light circuit) light emitted from second source diodes is polarized by the outer ring of the second polarizer filter.

A viewing polarizer is also provided positioned in the housing in line with viewing corridor of the optical lens. The viewing polarizer filters light reflected back from the skin and is cross-polarized relative to said first polarizer and is parallel-polarized relative to said second illumination source. Also, the housing in both embodiments is adapted to engage and be affixed to a camera body such that the lens of the camera can capture images of the object to be observed through said optical lens and viewing polarizer. A threaded recess in the viewing port of the device allows the device to mate with a standard camera lens to attach the device to the camera so that images of the examined skin can be captured. An adapter is additionally provided to mate the device with a camera where required. Also, both the second embodiments include a retractable spacer with a removable face plate with scale. In this regard the invention provides a user a choice between free-floating dry skin imaging and oil immersion to be used with the spacer.

BRIEF DESCRIPTION OF THE DRAWINGS

These as well as other features of the present invention will become more apparent upon reference to the drawings wherein:

FIG. 3 is a left side plan view of the device of the present invention;

FIG. 4 is a front plan view of the device of the present invention;

FIG. 5 is a bottom plan view of the device of the present invention;

FIG. 6 is a right side plan view of the device of the present invention;

FIG. 7 is a back plan view of the device of the present invention;

FIG. 8 is a top plan view of the device of the present invention;

FIG. 12 is perspective view of the lens assembly of the first embodiment of the present invention;

FIG. 13 is an exploded view of the lens assembly shown in FIG. 12;

FIG. 14 is a top plan view of the lens assembly shown in FIG. 12;

FIG. 15 is a cross-sectional view of the lens assembly along the A—A axis of FIG. 14;

FIGS. 16–18 are circuit diagrams of the various lighting and switch components of first embodiment of the present invention;

DETAILED DESCRIPTION OF THE INVENTION

The detailed description as set forth below in connection with the appended drawings is intended as a description of the presently preferred embodiments of the present invention, and does not represent the only embodiment of the present invention. It is understood that various modifications to the invention may be comprised by different embodiments and are also encompassed within the spirit and scope of the present invention.

Figure 1:
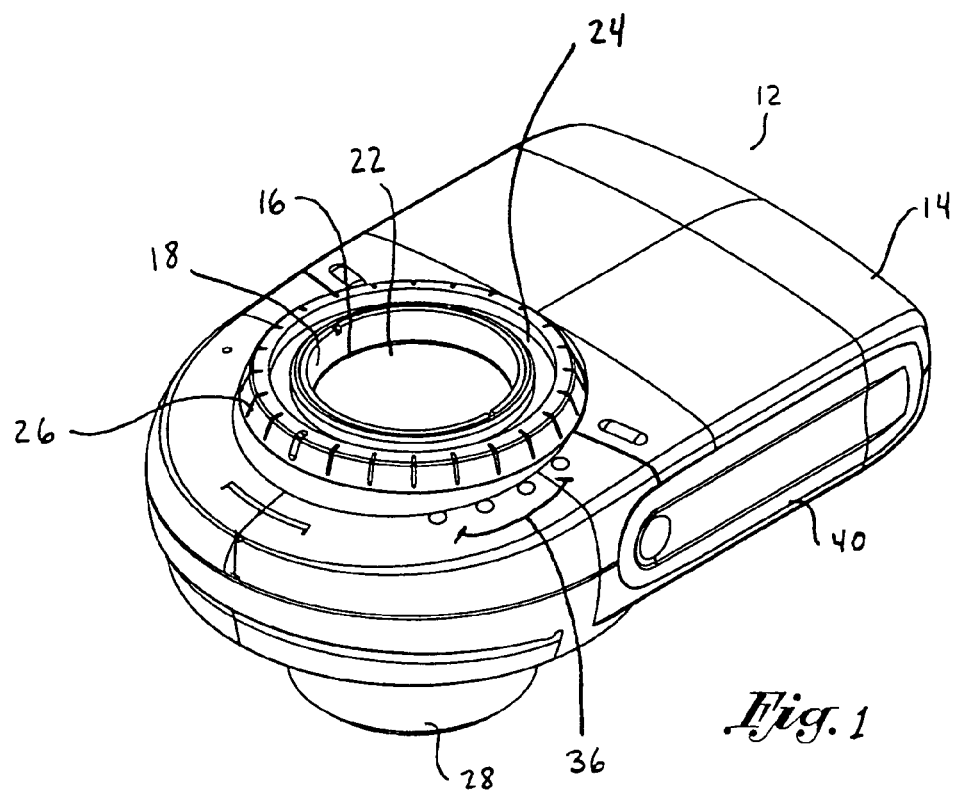
FIG. 1 is a is a front (proximal to the viewer) perspective view of the device of the present invention.
Figure 2:
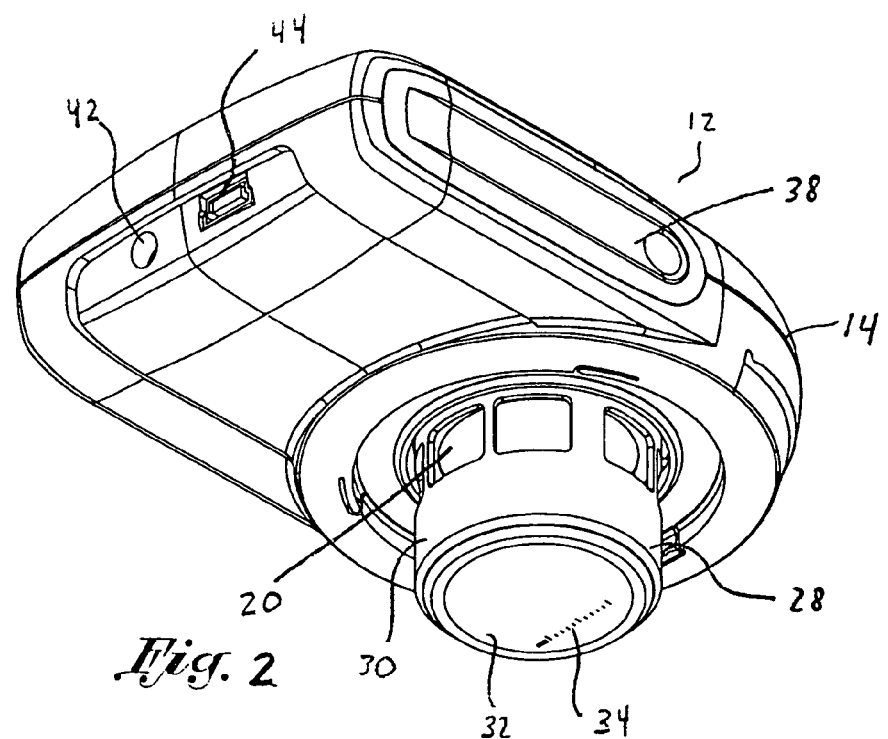
FIG. 2 is a back (proximal to the subject) perspective view of the device of the present invention.

Referring particularly to FIGS. 1 and 2, there are shown top and bottom perspective views, respectively, of the dermoscopy epiluminescence device 12 of the present invention. The device 12 is lightweight and compact. The outer structure of the device 12 can be utilized in association with the first embodiment (FIGS. 9–18), the second embodiment (FIGS. 19–27). The exterior appearance of the device for each of the first and second embodiments is identical as shown in FIGS. 1 through 8.

Referring collectively to FIGS. 1 through 8, the device 12 is shown with a housing 14 that encases the working components of the device. Preferably, the housing 14 is formed of assembled pieces of injection molded polycarbonate and polyurethane. It will be recognized by one skilled in the art that the housing 14 can be formed form other suitable rigid lightweight material, including, but not limited to plastic, composite materials, fiberglass, aluminum, PVC, acetate and or lexan. A distal viewing port 16 includes a lens retainer 18 for securing the lens and other internal components within the housing 14. The distal viewing port 16 is visually connected with the proximal viewing port 20 creating a line of sight through the housing 14 through lens 22 and polarizing filters (not shown). The view corridor through ports 16 and 20 allows a user to view with the skin with a naked eye to view subject skin placed below proximal viewing port 20.

A lens tube 24 secures the lens 22 and the entire lens assembly (not shown) within the housing 14. The exposed rim of the lens tube 24 includes threads (not shown) for engaging a standard cameral lens or a lens adaptor. In this regard, the device may be securely affixed to a camera, and the cameral can capture images through the corridor formed by the ports 16 and 20.

A circular dial 26 is exposed and is accessible about the perimeter of the distal viewing port 16. The dial may be manually rotated to effect a rotation of a spacer assembly (not shown) to extend or retract the spacer 28. With the spacer 28 retracted, the user can effect a dry examination of the skin. With the spacer 28 extended, a user can complete a direct contact skin examination, typically employing oil emersion. The spacer 28 includes a circular sidewall 30 that is retracted within the device when not in use, but extends outwardly and locks into place when extended. The sidewalls 30 support a glass faceplate 32. The glass faceplate 32 contacts the skin to be examined. The glass faceplate 32 also incorporates a scale 34 to provide the user with information regarding size of a lesion, blood vessel or other object to be viewed. The face plate 32 is removable from the spacer 28. The sidewalls 30 of the spacer 28 includes a plurality of openings to allow light projected from the illumination sources (not shown) to light the area to be examined.

Status LEDs 36 provide the user with information about the light set being used or the relative intensity of the lights. Side switches 38 and 40 provide the means to operate different sets of illumination sources (not shown) and to activate and deactivate light circuits. A power port 42 is provided as a means of powering the device or recharging on-board batteries (not shown). A USB port is provided as means of powering the device.

Figure 9:
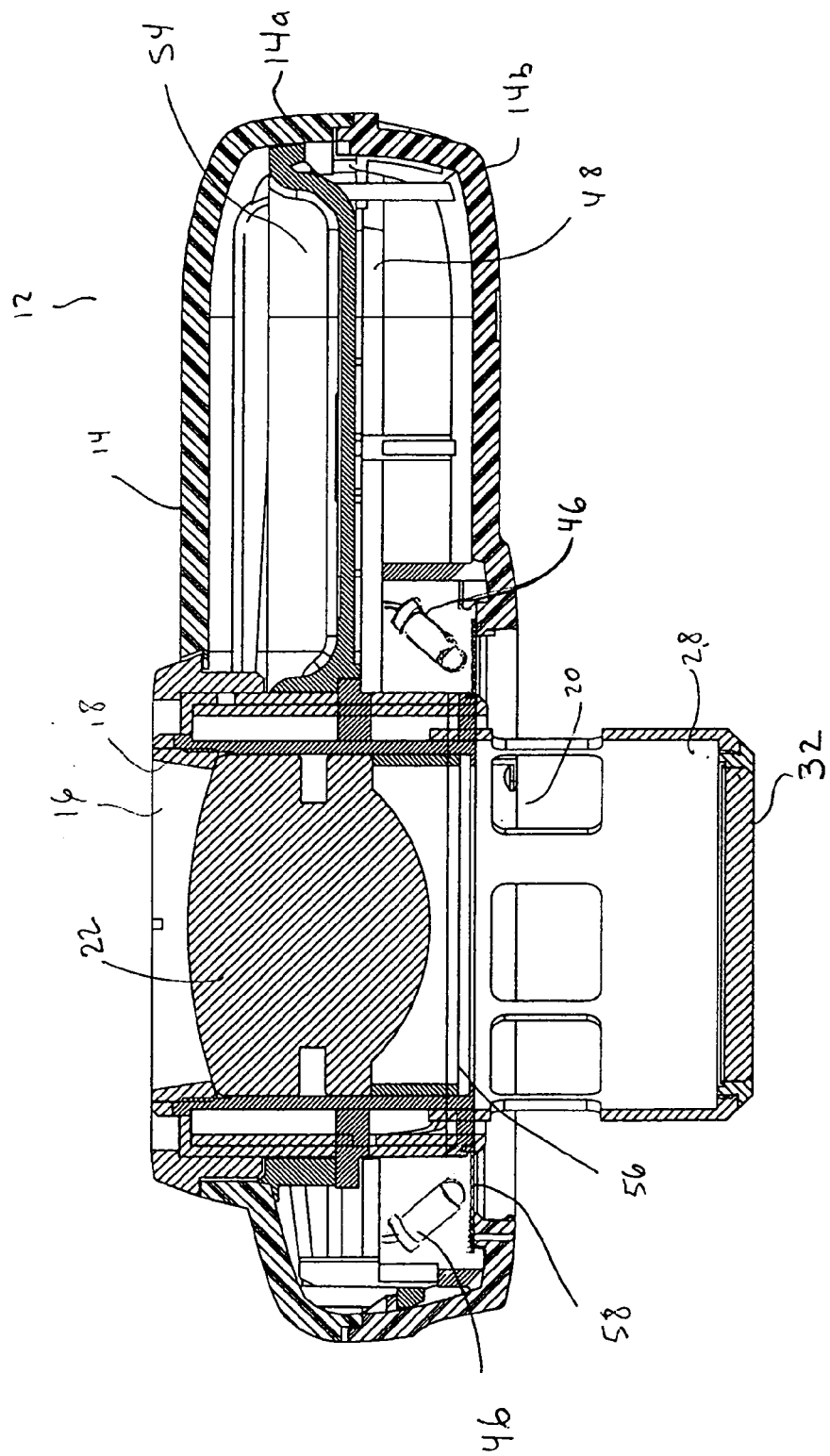
FIG. 9 is a cross-sectional view of the device of the present invention along the A—A axis as shown in FIG. 4.
Figures 10, 11:
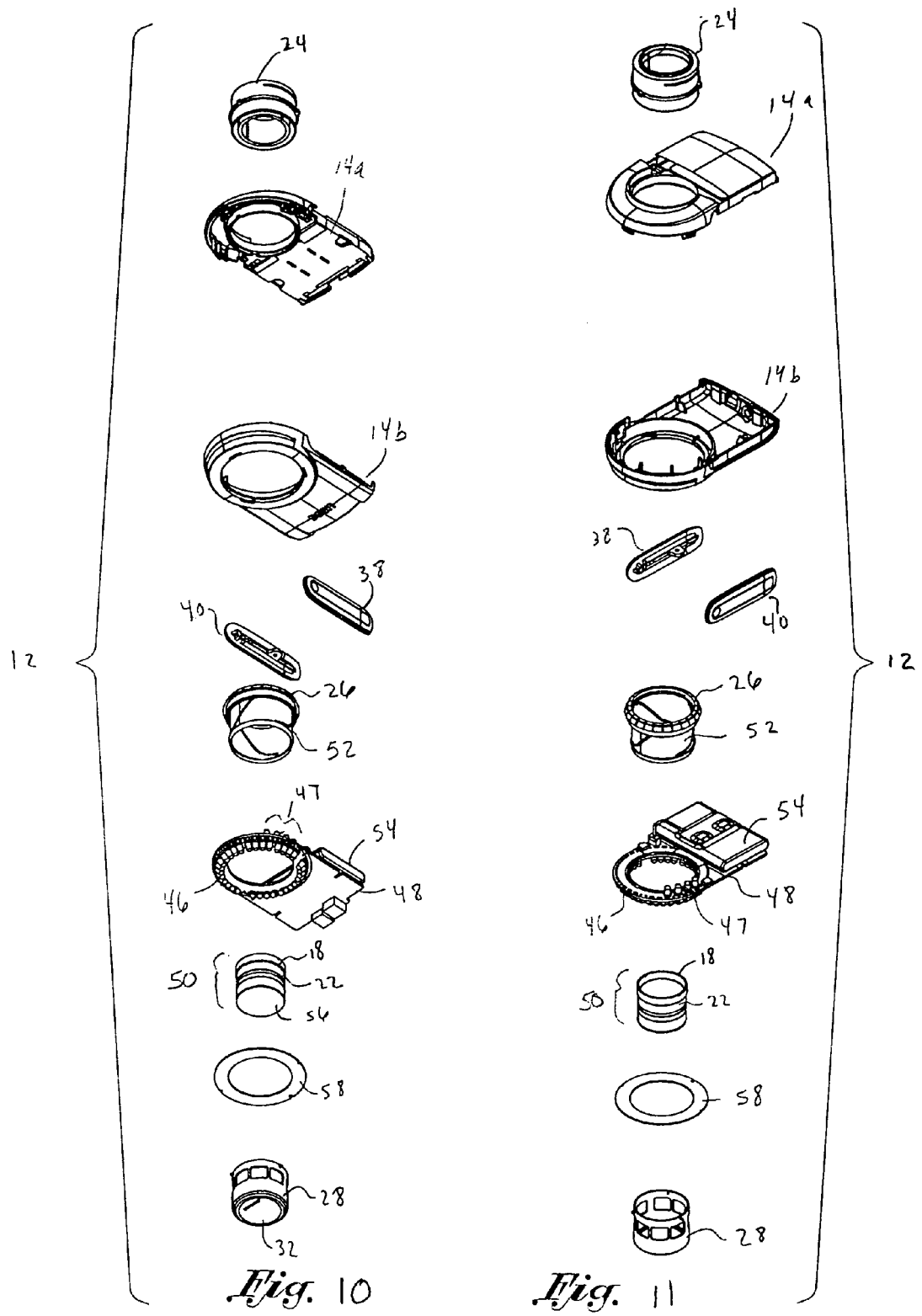
FIG. 10 is an exploded back view of a first embodiment of the present invention.
FIG. 11 is an exploded front of a first embodiment of the present invention.

Referring particularly to FIGS. 9–11, the device of a first embodiment of the present invention is shown. In FIG. 10 the device 12 is shown from a bottom perspective exploded view, and in FIG. 11 the device 12 is shown from a top perspective exploded view. The housing 14 is formed from top housing component 14a and bottom housing component 14b. Both components 14a and 14b include apertures for receiving a lens assembly 50, and accommodating a lighting array 46. The lighting array comprises a ring of LEDs affixed to an circuit board 48. The circuit board 48 is secured within the housing 14. The LEDs comprise four different colored sets of LEDs each on a different lighting circuit. The four colors comprise White, UV/Blue (405 nm), green/yellow (565 nm) and orange/red (630 nm). White is contemplated for normal epiluminescence imaging, U/Blue for ALA florescence and autoflouresence imaging an, green/yellow for superficial blood vessel imaging and orange/red for deeper blood vessel imaging. Although the invention contemplates use of the forgoing colors for the LEDs it is understood that other colors and combinations of colors are contemplated. For example, 480 nm, 580 nm and/or 660 nm may be used together or in combination with previously identified colors or in combination with colors not identified herein. Indicator LEDs provide the user information about the set of LEDs operating.

In the first embodiment, the LEDs of the lighting array 46 are four different colors, eight of each color for a total of 32 LEDs. The LEDs, are a repeating pattern of the four different colors, fore example, white, UV/blue, green-yellow and orange/red repeating around the perimeter, with all like colors interconnected on a single circuit. In operation, a user initiates a switch to light all of one color, which would comprise eight LEDs. The user can then immediately switch to a second colored set, and so forth. The user can compare and contrast images by toggling between colors. Although the first embodiment contemplates a repeating series of four different colored lights, it is also contemplated that other combinations and arrangements may be utilized. It is also contemplated that as few as two different colors may be used, or as many as thirty two sets of colors, or possibly more if a different number of LEDs are used. A battery 54 is selectively removable from the device 12 and the battery 54 electrically contacts the electrical board 48 and provides power to the device 12. The battery 54 is Lithium rechargeable battery is contemplated with greater than 600 mAh capability. The battery 54 is adapted for at least four hours of continuous use with 8 LEDs. A typical single lesion examination lasts one minute, and as such the battery life is expected to cover approximately 240 skin lesion examinations. Side switches 38 and 40 also interconnect with the board 48 and provide a user with the ability to selective operate the LEDs. The selection of the color of the LEDs of the light array 46 is done by switch 38 and the selection of the brightness of illumination is controlled by the swith 40. Power ON/OFF is controlled by depressing swich 40.

The lens 22 in the first embodiment is preferably a 25 mm diameter aspherical lens with a 10× optical gain. The aspherical design minimizes distortions. The lens is optimized to allow both visual viewing and also allow attachment of a digital camera for capturing images. A lens retainer 18 secures the lens 22 within the housing 14. Although the first embodiment employs a aspherical lens, the lens may be a single convex lens, a combination of two or more lenses, a double achromat lens, or a combination of double achromat lenses. In addition, the lens may incorporate Hastings lenses. The lenses are coated with an antireflection coating may be used and may additionally include a color filter to selectively filter light passing through the lens.

A lens assembly 50 is held within the lens tube 24. The lens tube 24 is received within the spacer mover 52. The spacer 28 is received over the spacer mover 52, such that the rotation of the spacer mover 52 within the housing 14 causes the spacer 28 to extend and retract. Rotation of the spacer mover 52 is manually operated by the dial 26.

A center polarizer 56 is integrated with the lens assembly 50, and provides polarization to the eye of the user (or to a camera lens). An outside ring polarizer 58 provides polarization to of light from the lighting array 46, and such ring polarizer 58 is 90 degrees out of phase with the center polarizer 5 The center polarizer 56 and outer ring polarizer 58 are composed of acrylic plastic with polarization material embedded within the polarizer. It is contemplated by the invention that the polarizers 56 and 58 may be constructed of glass, also with material embedded or coated on the glass. In addition, the polarizers 56 and 58 may be coated with a filter material that can selectively filter out some of the light frequencies emanating from the object. Alternatively, the secondary filter assembly made of plastic or glass with the capability of filtering the light may be placed in the path of the lens 22 to filter out some of the light. 6 such that the light that reaches the eye of the user (or the camera lens) is cross-polarized. It is contemplated by the present invention that the center polarizer 56 and ring polarizer may be selectively removable, to aid in viewing certain oil immersion dermoscopy examinations. It is also contemplated that device of the present invention can be produced without any polarizing filters.

Referring particularly to FIGS. 13–15, there is shown the lens assembly 50 combined with the spacer components to form the lens-spacer assembly 60. The lens assembly comprises a lens retainer 18, to retain the lens 22. A polarizer spacer 62 is provided below the lens 22. A center polarizer 56 is placed over the circular polarizer spacer 62. The lens assembly 50 is placed within the lens sleeve 24. At the base, an outside polarizer 58 is provided to provide polarization to the lighting array 46.

Figure 17:
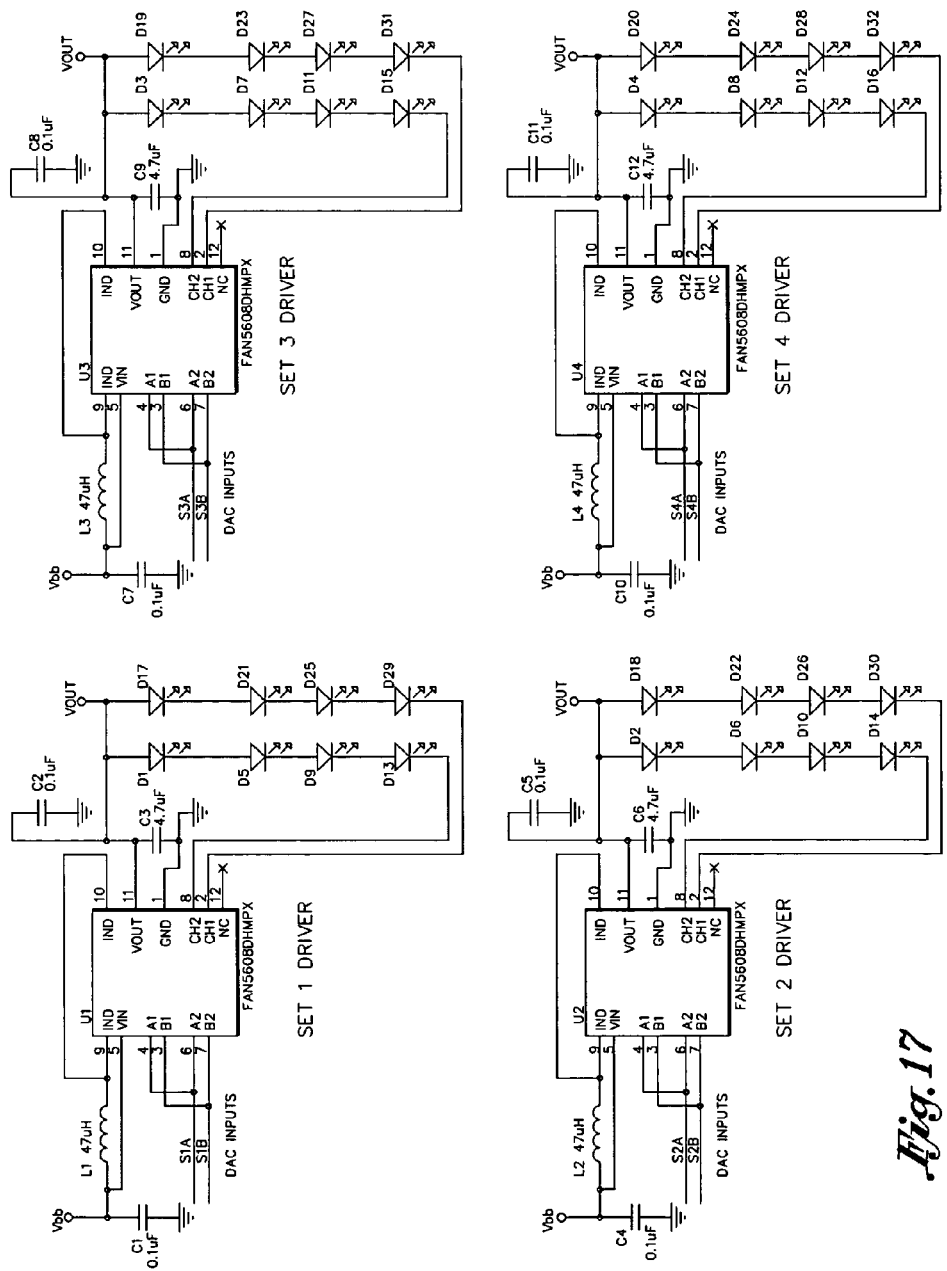
Figure 18:
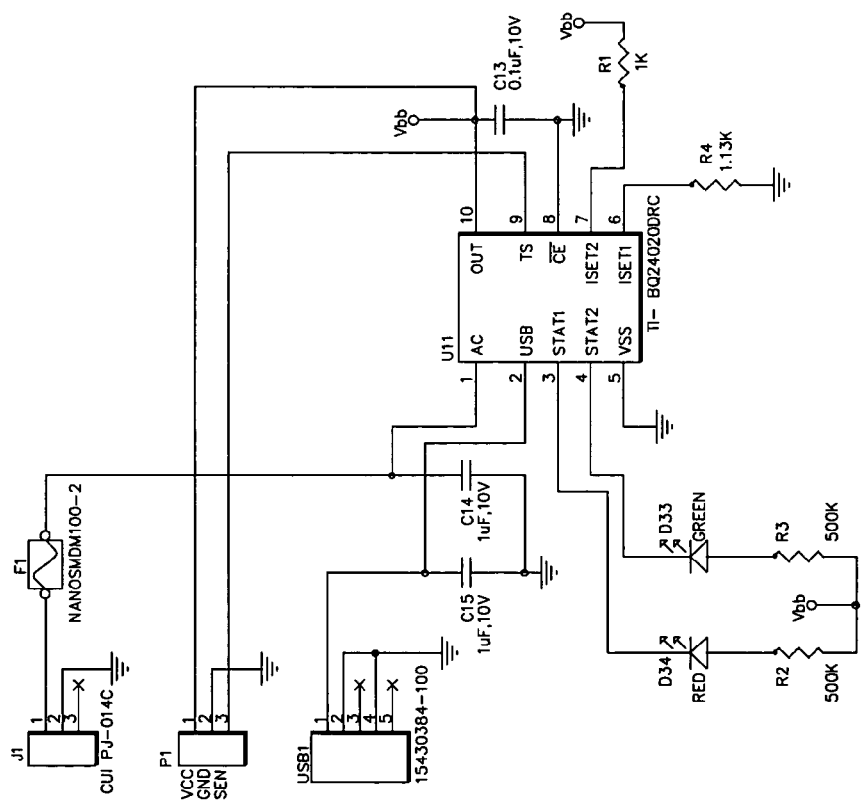
Figure 19:
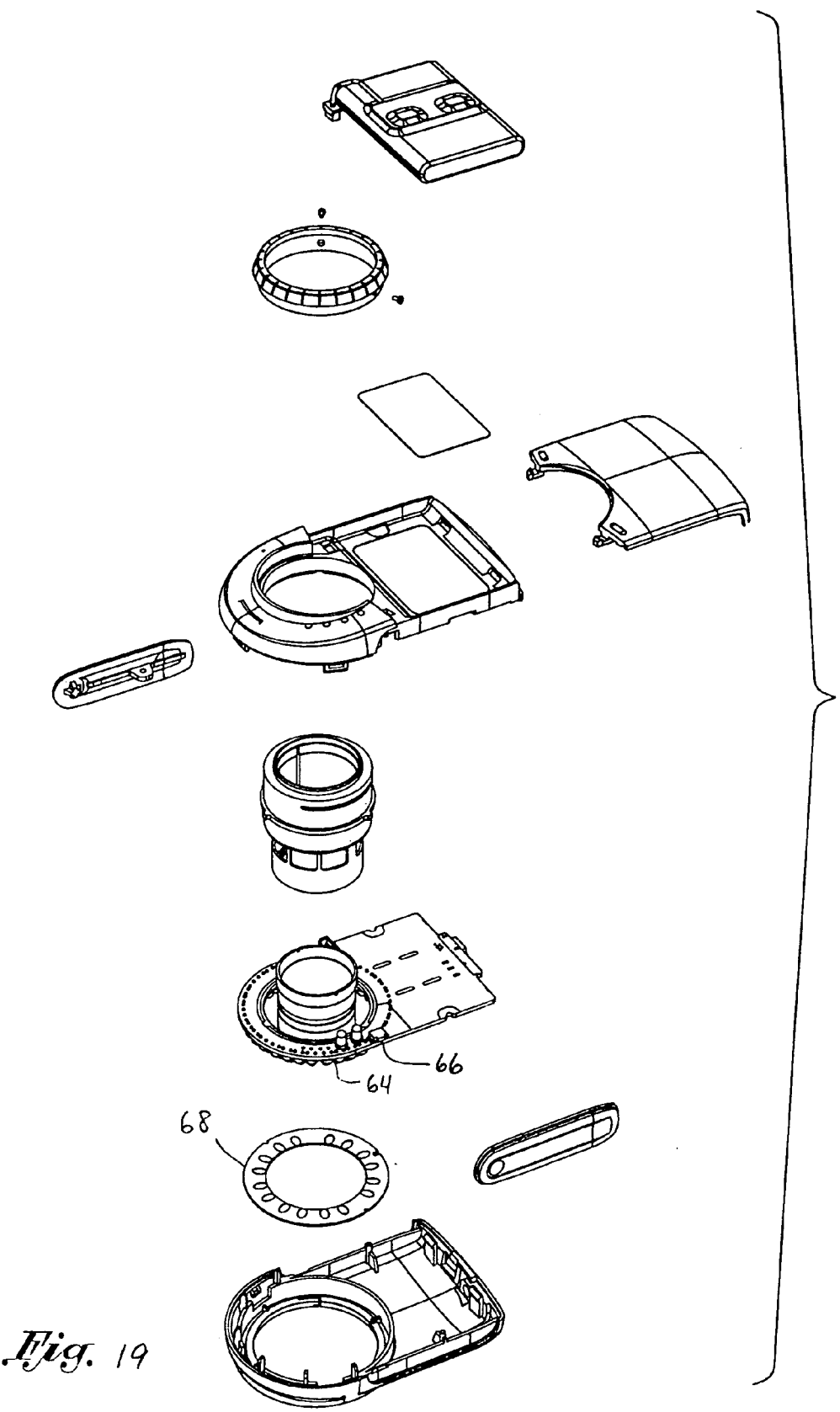
FIG. 19 is an exploded view of a second embodiment of the present invention.
Figure 20:
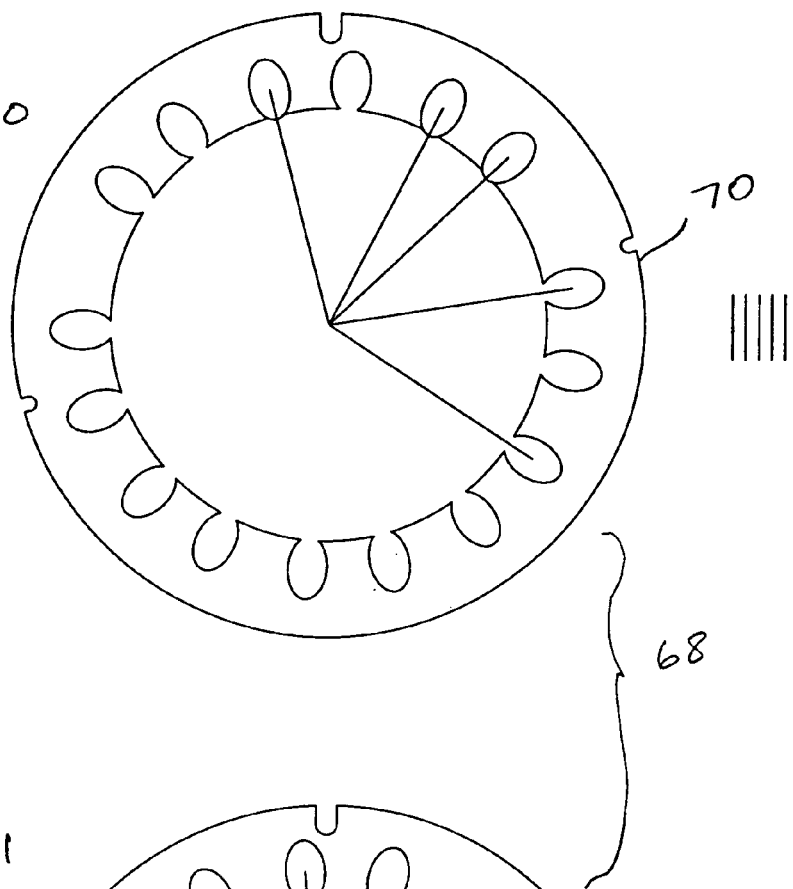
FIG. 20 is a plan view of a first polarizing filter of the second embodiment of the present invention showing the angle of polarization.
Figure 21:
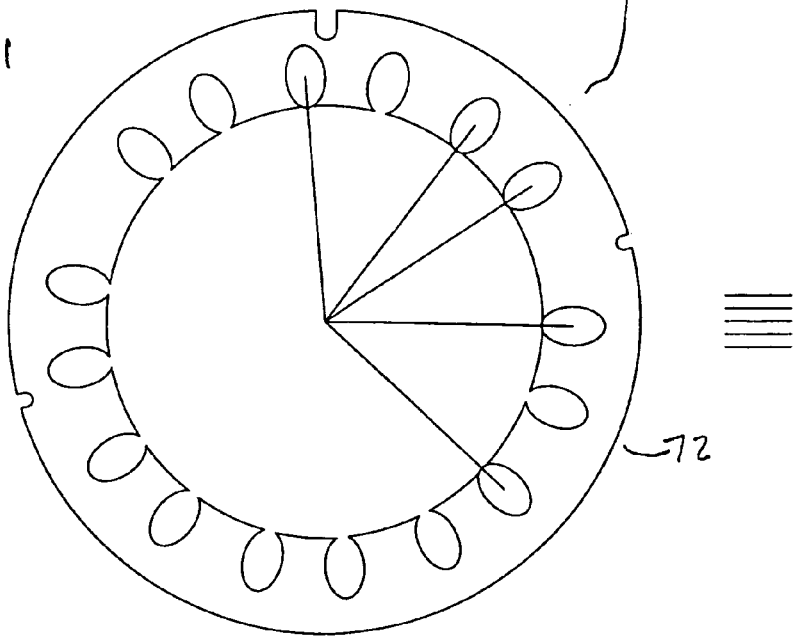
FIG. 21 is a plan view of a second polarizing filter of the second embodiment of the present invention showing the out of phase polarization as compared to the first polarizing filter.
Figure 22:
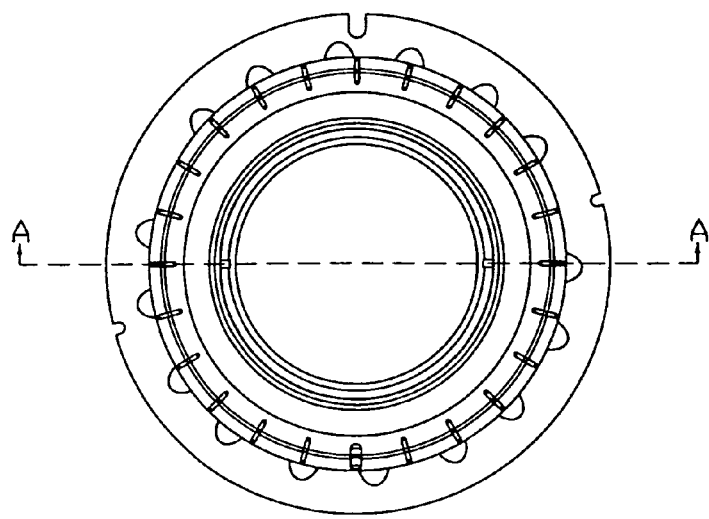
FIG. 22 is a top plan view of the lens assembly of the second embodiment of the present invention.
Figure 23:
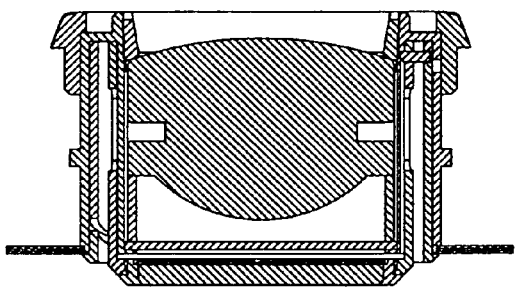
FIG. 23 is a cross-sectional view of the lens assembly along the A—A axis as shown in FIG. 22.
Figure 24:
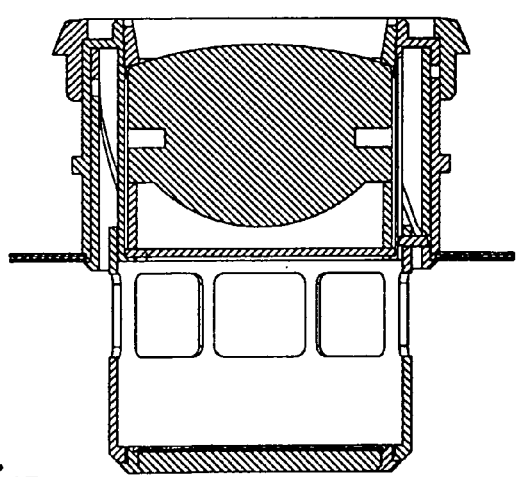
FIG. 24 is a cross-sectional view of the lens assembly along the A—A axis as shown in FIG. 22 with the spacer extended.
Figures 25, 26, 27:
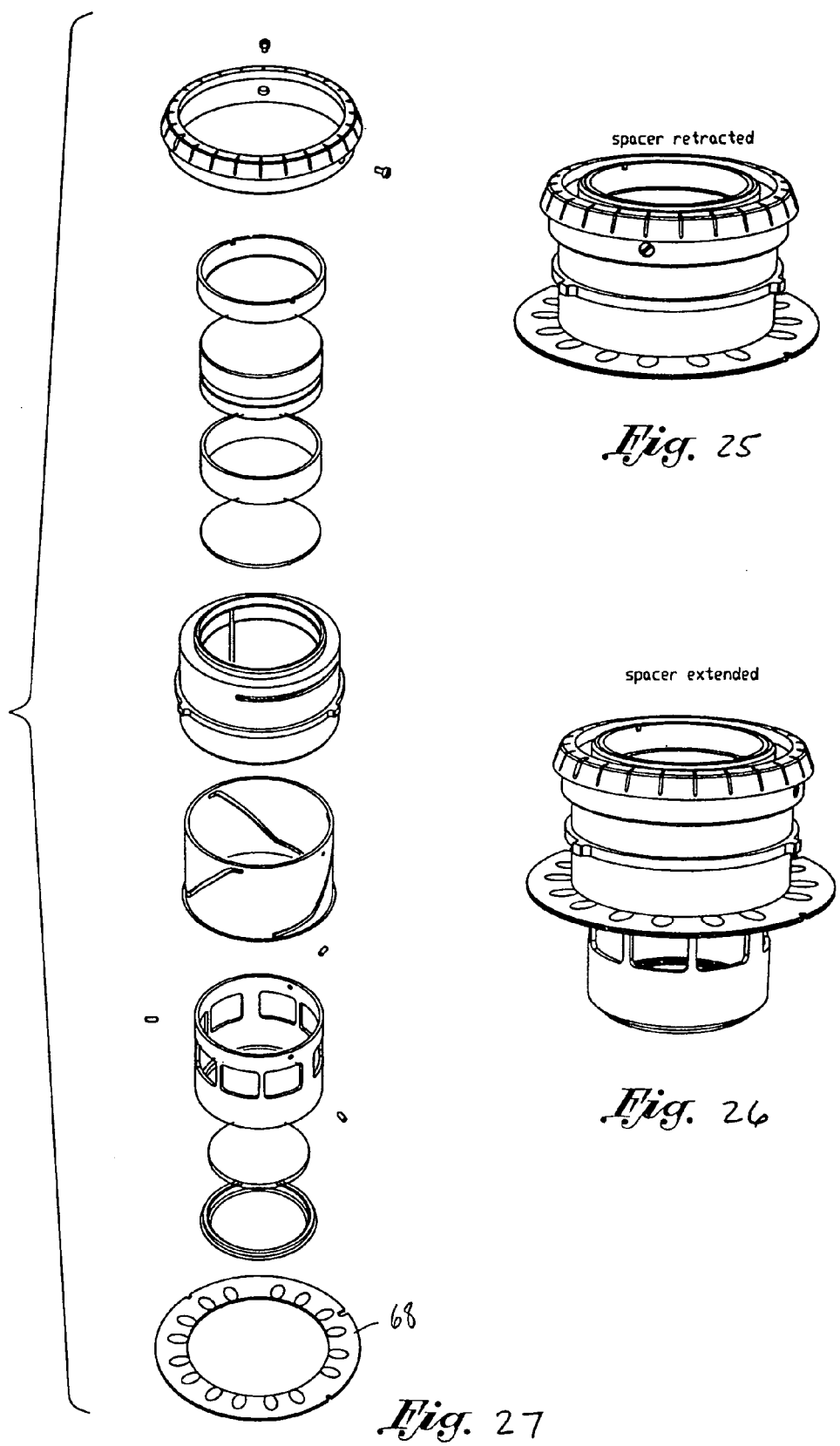
FIG. 25 is a perspective view of the lens assembly of the device of the second embodiment.
FIG. 26 is a perspective view of the lens assembly of the device of the second embodiment, with the spacer extended.
FIG. 27 is an exploded view of the lens assembly as shown in FIGS. 25–26.

FIGS. 16–18 represent the lighting circuits used to power the lighting array 46 of the device 12. It is contemplated that the lighting circuits may be comprised of any different number of circuit designs and the circuits represented in FIGS. 16–18 are one way of completing the function of the lighting circuits. Other schemes and designs are contemplated for controlling the lights and selection of color, including, but not limited to, remote control by a USB connector and an on-board microprocessor, control by embedded software in on-board electronics and computer controlled by the USB connector.

FIGS. 19–27 represent the second embodiment of the present invention and are referred hereto collectively. The design of the second embodiment is nearly identical to the first embodiment (and thus the description of common elements are not repeated herein) except for the following differences. In the second embodiment, the lighting array 64 comprises two sets of LEDs, both sets white light. In this regard only two indicator LEDs 66 are required. Also, the outside filter 68 comprises two ring filters 70 and 72, each filter 90 degrees out of phase with the other. In conformance with two sets of lights, the lighting circuits (not shown) are modified for the second embodiment.

The top 70 and bottom 72 polarizers are 90 degrees out of phase. The bottom 72 polarizer is in cross polarization with the center polarizer 56 and top polarizer 70 is in parallel polarization with the center polarizer 56. The top 70 and bottom 72 polarizers are composed of acrylic plastic and include polarization at different angles. The polarizers 70 and 72 may also be coated with a special material to filter out some of the light emanating from the LEDs, or alternatively the annular polarizer 70 and 72 may be sandwiched with a color filter acrylic material. The aperture of the polarizer 58 is wide enough to permit a viewing corridor from the lens 22 through the housing 14 while allowing portions of the top 70 and bottom 72 polarizers to be exposed and to filter light emitting diodes inside the housing 20.

Thirty two light emitting diodes of the array 46 ring the circuit board. The diodes are preferably white high light output Indium Gallium Nitride LEDs, however any suitable lighting diodes are appropriate. The even diodes are on a single circuit and the odd diodes are on a separate single circuit. In the second embodiment, the LEDs are a standard white LED made with phosphorescence phosphors to create white light. It is additionally contemplated by the present invention that tricolored LEDs, with individual red, green and blue LEDs that can combine form white light may be utilized. It is contemplated by the present invention that the LEDs may have focusing lenses to concentrate the light into a smaller and tighter beam. The LEDs may additionally be comprised of indium gallium arsenide material, or any other like semiconductor material. A switch may initiates half of the every other light source, which are the eight even diodes and the switch also initiates the second light source, which are the other sixteen odd diodes. All 32 diodes of the array 46 may be simultaneously A first polarizer filter 70 comprises a planar annular ring defining a generally circular center opening and an outer ring. The center opening of the annular ring of the first polarizer 70 is positioned in alignment with the circular optical lens 22 to provide an unobstructed view of the skin through the lens 22 and the housing 14. The outer ring of the first polarizer 70 includes a plurality of openings sized and positioned to correspond to the diodes of the second illumination source (i.e. every other diode 58 of the second light circuit) such that light emitted from the diodes of the second illumination source passes through the openings unfiltered by the first polarizer 70. Because there are no corresponding openings for the diodes of the first illumination source (i.e. every other diode on the first light circuit) light emitted from first source diodes is polarized by the outer ring of the first polarizer filter 50.

A second polarizer filter 72 comprises a planar annular ring defining a generally circular center opening and an outer ring. The center opening of said annular ring of the second polarizer 72 is positioned in alignment with the circular optical lens 22 to provide an unobstructed view of the skin through the lens 22 and housing 14. The second polarizer 72 is 90 degrees out of phase with the first polarizer 70. The outer ring of the second polarizer 52, like the first polarizer 50, has a plurality of openings sized and positioned to correspond to the diodes of the first illumination source (i.e. every other diode on the first light circuit) such that light emitted from the diodes of the first illumination source passes through the openings unfiltered by the second polarizer 72. Because there are no corresponding openings for the diodes 58 of the second illumination source (i.e. every other diode on the second light circuit) light emitted from second source diodes is polarized by the outer ring of the second polarizer 72. While the only two light sources (i.e. two sets of diodes) are contemplated three or more sets of diodes are contemplated by the second embodiment of the present invention.

It should be noted and understood that with respect to the embodiments of the present invention, the materials suggested may be modified or substituted to achieve the general overall resultant high efficiency. The substitution of materials or dimensions remains within the spirit and scope of the present invention.

What is claimed is:

1. A dermoscopy epiluminescence device comprising:
   a) a generally circular optical lens defining an outer circumference to produce a magnified image of an object to be observed by a viewer;
   b) an illumination source comprising a plurality of luminous diodes spaced about the circumference of said optical lens to direct light upon the object;
   c) at least one polarizer comprising a planar annular ring filter defining a generally circular center opening and an outer ring, said center opening of said annular ring is positioned in corresponding alignment with the circular optical lens to provide an open view of the object through the lens, said outer ring having at least one opening sized and positioned to correspond to at least one of the diodes of the illumination source of a first colored wavelength such that light emitted from said at least one diode of the illumination source is passed through said at least one opening toward the object and light emitted from remaining diodes of a second colored wavelength of the illumination source is polarized by the polarizer;
   d) a viewing polarizer positioned between a viewer and the object to polarize light reflected from the object wherein said viewing polarizer is cross-polarized relative to polarized light emitted from said remaining diodes; and e) at least one switch for initiating diodes of a first colored wavelength at a first position and for initiating diodes of a second wavelength at a second position.

2. The dermoscopy epiluminescence device of claim 1 further comprising a power source to power said illumination sources.

3. The dermoscopy epiluminescence device of claim 2 wherein said power source is a battery.

4. The dermoscopy epiluminescence device of claim 2 wherein said power source is a lithium battery.

5. The dermoscopy epiluminescence device of claim 2 wherein said power source is a USB connection.

6. The dermoscopy epiluminescence device of claim 1 wherein at least one of said luminous diodes are white light emitting diodes.

7. The dermoscopy epiluminescence device of claim 1 wherein at least one of said luminous diodes are high light output Indium Gallium Nitride light emitting diodes.

8. The dermoscopy epiluminescence device of claim 1 wherein said optical lens is a Hastings Triplet lens.

9. The dermoscopy epiluminescence device of claim 1 wherein said optical lens is a 15 mm diameter Hastings lens with a 10× optical gain.

10. The dermoscopy epiluminescence of claim 1 further comprising, a housing for integrating the optical lens, illumination source, polarizer and viewing polarizer and wherein said housing is adapted to selectively employ a spacer between the housing and the object to be viewed allowing a user to conduct direct contact examination with the spacer employed and non-contact examination when the spacer is not employed.

11. A dermoscopy epiluminescence device comprising:

a) a generally circular optical lens defining an outer circumference to produce a magnified image of an object to be observed by a viewer;

b) an illumination source comprising a plurality of luminous diodes spaced about the circumference of said optical lens to direct light upon the object;

c) at least one a polarizer comprising a planar annular ring filter defining a generally circular center opening and an outer ring, said center opening of said annular ring is positioned in corresponding alignment with the circular optical lens to provide an open view of the object through the lens, said outer ring having at least one opening sized and positioned to correspond to at least one of the diodes of the illumination source such that light emitted from said at least one diode of the illumination source is passed through said at least one opening toward the object and light emitted from remaining diodes of the illumination source is polarized by the polarizer;

d) a viewing polarizer positioned between a viewer and the object to polarize light reflected from the object wherein said viewing polarizer is cross-polarized relative to polarized light emitted from said remaining diodes; and e) a housing for integrating the optical lens, illumination source, polarizer and viewing polarizer and wherein said housing is adapted to selectively employ a spacer between the housing and the object to be viewed allowing a user to conduct direct contact examination with the spacer employed and non-contact examination when the spacer is not employed.

12. The device of claim 11 wherein said direct contact examination utilizes oil emersion.

13. The device of claim 11 wherein said device is adapted to interface with a USB connection.

14. The device of claim 13 wherein said housing further incorporates a USB port.

15. The device of claim 11 wherein said housing further incorporates an on-board microprocessor.

16. The device of claim 11 wherein said housing is further adapted to engage and be affixed to a camera body.

17. The device of claim 11 where said spacer is affixed to said housing and is retractable to conduct non-contact examination and extendable to a locked position for direct contact examination.

18. A selective polarization device for producing a polarized view of an object to be observed by a viewer, the device comprising:

a) an optical lens defining an outer circumference;

b) a plurality of first and second luminous diodes being alternately spaced about said outer circumference to form a ring of diodes;

c) at least one a polarizer comprising an annular ring filter defining a generally circular center opening, an outer ring and a plurality of openings, said center opening corresponding with the optical lens to provide an open view of the object through the lens, said outer ring substantially corresponding to said outer circumference, said plurality of openings being sized and positioned corresponding to said second diodes with light emitted therefrom being transmittable through the openings toward the object and light emitted from said first diodes being polarized by the polarizer;

d) a viewing polarizer being positioned between said viewer and being cross-polarized relative to said polarizer; and e) a housing for integrating the optical lens, said plurality of first and second luminous diodes, polarizer and viewing polarizer and wherein said housing is adapted to selectively employ a spacer between the housing and the object to be viewed allowing a user to conduct direct contact examination with the spacer employed and non-contact examination when the spacer is not employed.

19. The device of claim 18 wherein said direct contact examination utilizes oil emersion.

20. The device of claim 18 wherein said device is adapted to interface with a USB connection.

21. The device of claim 18 wherein said housing further incorporates a USB port.

22. The device of claim 18 wherein said housing further incorporates an on-board microprocessor.

23. The device of claim 18 wherein said housing is further adapted to engage and be affixed to a camera body.

24. The device of claim 18 where said spacer is affixed to said housing and is retractable to conduct non-contact examination and extendable to a locked position for direct contact examination.

* * * * *